United States Patent [19]

Dieras et al.

[11] Patent Number: 4,804,364

[45] Date of Patent: Feb. 14, 1989

[54] APPARATUS FOR THE CURETTAGE OR EXERESIS OF BIOLOGICAL TISSUES BY MEANS OF AN INSTRUMENT VIBRATING AT ULTRASOUND FREQUENCIES

[75] Inventors: Francis Dieras, Bordeaux; Alain Soulie, Cestas; Jean-Louis Larrieu, Lanton; Bernard Escanecrabe, Villenave D'Ornon, all of France

[73] Assignee: SATELEC, Merignac, France

[21] Appl. No.: 40,996

[22] PCT Filed: Jul. 21, 1986

[86] PCT No.: PCT/FR86/00256

§ 371 Date: May 18, 1987

§ 102(e) Date: May 18, 1987

[87] PCT Pub. No.: WO87/00422

PCT Pub. Date: Jan. 29, 1987

[30] Foreign Application Priority Data

Jul. 19, 1985 [FR] France ................................ 85 11106

[51] Int. Cl.⁴ .................... A61M 1/00; A61B 17/20
[52] U.S. Cl. .................................... 604/22; 128/305;
128/303.1; 433/86; 433/119
[58] Field of Search ................ 128/24 A, 24.1, 303.1,
128/305; 433/86, 118, 119; 604/22

[56] References Cited

U.S. PATENT DOCUMENTS

| Re. 25,033 | 8/1961 | Balamuth et al. | 433/119 X |
|---|---|---|---|
| 3,805,787 | 4/1974 | Banko | 604/22 |
| 3,809,977 | 5/1974 | Balamuth et al. | 433/86 X |
| 4,223,676 | 9/1980 | Wuchinich et al. | 433/86 X |
| 4,316,465 | 2/1982 | Dotson, Jr. | 128/305 |
| 4,428,748 | 1/1984 | Peyman et al. | 604/22 |

FOREIGN PATENT DOCUMENTS 3422628 12/1985 Fed. Rep. of Germany ...... 433/119

Primary Examiner—Samuel Scott
Assistant Examiner—Allen J. Flanigan
Attorney, Agent, or Firm—McAulay, Fields, Fisher, Goldstein & Nissen

[57] ABSTRACT

Ultrasound apparatus intended for the curettage or exeresis of biological tissues by irrigation of a liquid subject to cavitation and by suction of the disaggregated tissues, the apparatus comprising a hand-piece containing a transducer which is mechanically coupled to a vibrating instrument or sonotrode. Said apparatus is characterized in that the handpiece (1) is traversed in the longitudinal direction by a section conduit (15,24) connected on the one hand to a suction connector (3) provided at the backend of the end piece (1), and one the other hand to the internal part of the suction sonotrode (17).

11 Claims, 2 Drawing Sheets

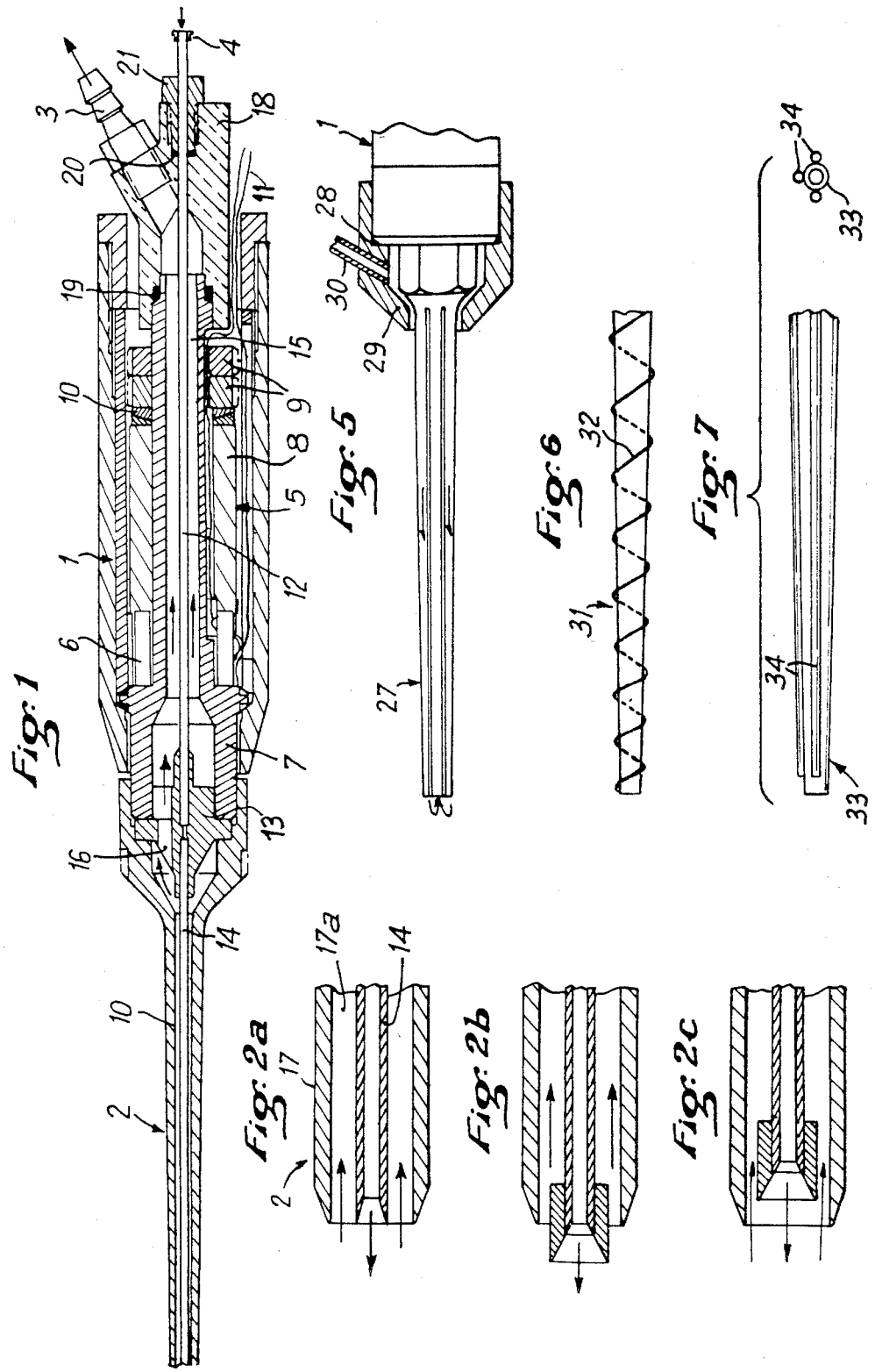

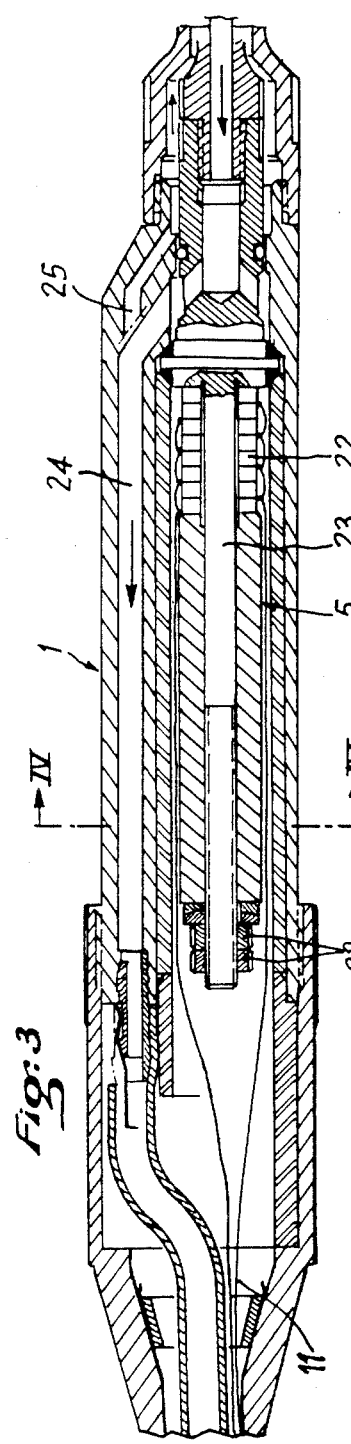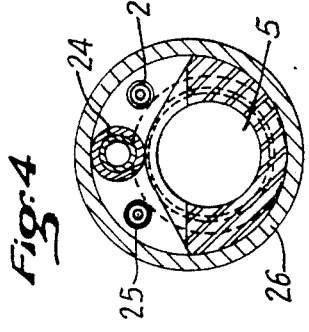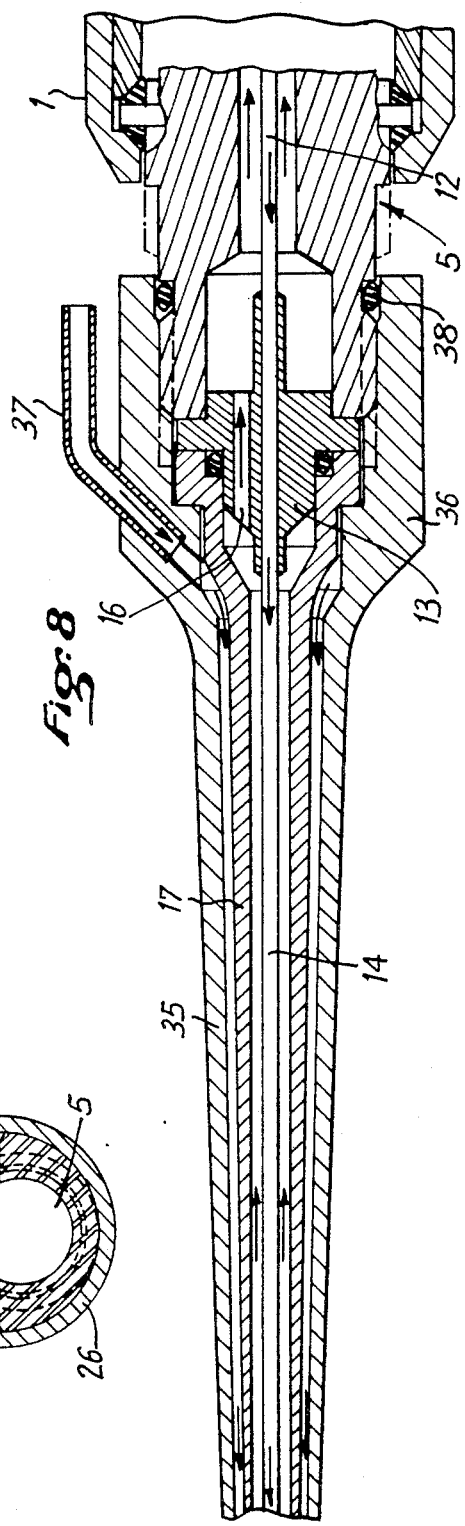

APPARATUS FOR THE CURETTAGE OR EXERESIS OF BIOLOGICAL TISSUES BY MEANS OF AN INSTRUMENT VIBRATING AT ULTRASOUND FREQUENCIES

The present invention relates to an apparatus for the curettage or exeresis of biological tissues by an instrument vibrating at ultrasound frequencies, associated with one or more irrigating fluids placed in cavitation and absorbed by a coaxial suction system.

Apparatus using ultrasounds for the treatment of surfaces have been proposed for a long time. This is the case in industry, as in the medical field, particularly in dental surgery. The extreme rapidity of the ultrasound vibrations transmitted to an instrument makes it possible to detach and reduce into fine particles deposits such as tartar.

Such an apparatus is all the more efficient as a projection of fluid or of abrasive powder can be added thereto, which erodes the part to be detached which may then be recovered by a suction system.

Such a combination of means, namely projection of particles or of fluid(s), ultrasounds applied to a tool and suction, is moreover described in U.S. Pat. No. 2,874,470. This patent demonstrates the interest of this combination, for its efficiency and for its ergonomic advantages.

The present invention takes up the combination of these means, irrigation and suction, adopting for each of these functions a coaxial configuration such as may be seen in U.S. Pat. No. 2,709,852 which describes a dental apparatus, or in U.S. Pat. No. 3,089,790, which describes a cleaning apparatus employing ultrasounds, with coaxial irrigation and suction.

In the surgical domain, apparatus do exist which take up this type of configuration in the same manner and use the same combination of means. However, these apparatus, known under the name of ultrasound surgical aspirators, present a certain number of drawbacks.

On the one hand, the hand-piece does not entirely integrate the circuits of the fluids, particularly the suction conduit and the irrigation conduit with, as consequence, an exaggerated increase in the diameter of this hand-piece. Any delicate operation is thus rendered difficult and tiring for the operator. The magnetostriction used in the known apparatus does not enable these drawbacks to be overcome.

On the other hand, the known technique of ultrasound surgical suction has the drawback of tearing the tissues in certain cases, in particular in the case of the suction being poorly adjusted. Conversely, in other cases, the destroying effect is insufficient and the process presents risks for the adjacent tissues in the case of exeresis of certain tumours, particularly cystic ones.

In such a known apparatus, there is no other solution, in the difficult cases requiring a highly efficient apparatus, than the reinforcement of the suction or of the ultrasounds applied to the single vibrating instrument also called "sonotrode". In this latter case, the power may be such that heating is considerable and the amplitude obtained at the end of the sonotrode may damage the adjacent tissues and vessels.

To this end, this ultrasound apparatus for the curettage or exeresis of biological tissues by irrigation of a liquid subjected to cavitation and by suction of the disaggregated tissue, comprising a hand-piece containing a transducer which is mechanically coupled to a vibrating instrument or sonotrode, is characterized in that the hand-piece is traversed right through, in the longitudinal direction, by a suction conduit connected on the one hand to a suction connector located at the rear end of the hand-piece and, on the other hand, to the internal part of the suction sonotrode.

The apparatus according to the invention has the advantages:

of integrating the circuits of the fluids from one end of the hand-piece to the other, offering the possibility of having a large suction diameter;

of lightening to a maximum this hand-piece which is like a tube;

of having, thanks to the high yield of the piezo-electricity, a minimum heating of the assembly. Thanks to an automatic adaptation of the amplitude of the vibration of the hand-piece as a function of the resistance of the tissue encountered, it is possible to act efficiently on any sort of tissue.

It is possible to use either washers in piezo-electric ceramics polarized in the thickness, or a tube of piezo-electric ceramics polarized radially, this having for advantage to clear to a maximum the very interior of the transducer. This advantage makes it possible to be able to combine an assembly of means, including suction and irrigation, in a restricted volume, but it also enables other means such as a sight for optical fiber and/or a laser beam, to be coaxially integrated.

The use of several sonotrodes fixed on the same transducer makes it possible to modulate the cutting effect and to avoid any risk of tissue tear. The effect of cavitation is considerable due to the integration of the irrigation fluid in a sonotrode.

Various embodiments of the present invention will be described hereinafter by way of non-limiting examples, with reference to the accompanying drawing, in which:

FIG. 1 is a view in axial section of an apparatus according to the invention.

FIGS. 2a, 2b, 2c are views in partial axial section of various embodiments of the end parts of the sonotrodes.

FIG. 3 is a view in axial section of a simplified variant embodiment of a hand-piece.

FIG. 4 is a view in transverse section made along line IV—IV of FIG. 3.

FIG. 5 is a view in elevation of a single sonotrode with outside longitudinal flow of the irrigation fluid.

FIG. 6 is a schematic view in elevation of a variant embodiment of a sonotrode with outside helical flow of the irrigation fluid.

FIG. 7 is a schematic view in elevation of another variant embodiment of a sonotrode with outside longitudinal flow of the irrigation fluid.

FIG. 8 is a view in partial axial section of a variant embodiment of the apparatus.

The apparatus according to the invention shown in FIG. 1 comprises, in conventional manner, a hand-piece 1 containing a generator of ultrasound vibrations or transducer 5 extended, at its front end, by an elongated instrument 2 subjected to axial ultrasound vibrations and constituted by one or more coaxial sonotrodes. At its rear end, the hand-piece 1 bears connectors, namely a connector 3 connected to a source of vacuum, in order to effect suction, and a connector 4 for admission of an irrigation fluid.

The transducer 5 comprises a tube 6 of piezo-electric ceramics which is maintained blocked between a front part 7, of relatively large diameter, and a distance piece 8 blocked by means of tightening nuts 9, the tightening pressure being ensured by two prestress washers 10. The piezo-electric tube 6 is connected to the outside by electric connecting wires 11 which emerge from the rear end of the hand-piece 1. As may be seen in FIG. 1, the central part of the transducer 5 is hollow and it allows the through passage, through the hand-piece 1, of an irrigation fluid and of the suction current. In the non-limiting embodiment shown in FIG. 1, the transducer is axially traversed right through by an axial irrigation tube 12 which is connected, at its rear end, to the connector 4 for admission of the irrigation fluid. This irrigation tube 12 is fast with the front part 7 of the transducer 5 so as to be subjected to the ultrasound vibrations, and this via a connecting piece 13. This connecting piece 13 is pierced right through with a central conduit and it is connected, at its front part, to an axial tube 14 extending over the whole length of the vibrating instrument 2. This tube 14 thus constitutes an irrigation sonotrode of the apparatus.

Furthermore, the transducer 5 is traversed, right through, in the axial direction, by at least one suction conduit 15 which is offset outwardly with respect to the irrigation tube 12 and which communicates with the suction connector 3. In the example illustrated in the drawing, the suction conduit 15 is constituted by the internal volume of the transducer 5 which surrounds the central irrigation tube 12. This suction conduit 15 communicates, via at least one hole 16 pierced right through the connecting piece 13, with at least one suction conduit extending longitudinally inside the wall of the vibrating instrument 2 which forms the suction sonotrode. The inner conduit of the suction sonotrode 17 is in fact constituted, in this embodiment, by the volume surrounding the central conduit of the irrigation sonotrode 14.

In the rear part of the hand-piece 1 is housed a connecting block 18 which is connected to the rear end of the transducer 5, with interposition of an O-ring 19 and which is traversed axially by the rear part of the irrigation tube 12 extending up to the irrigation connector 4. Another O-ring 20 is disposed in the connecting block 8 around the irrigation tube 12 and it is maintained tightened by a stuffing box 21 traversed by the irrigation tube 12 and screwed in the rear part of the connecting block 18.

The two irrigation sonotrodes 14 and suction sonotrode 17 may terminate, at their front ends, either in the same transverse plane as illustrated in FIG. 2a, or in different transverse planes. In the case illustrated in FIG. 2b, the internal irrigation sonotrode 14 projects with respect to the outer suction sonotrode 17 whilst FIG. 2c shows the reverse arrangement in which the outer suction sonotrode 17 extends beyond the internal irrigation sonotrode 14. Furthermore, FIGS. 2a, 2b and 2c show that the end parts of the sonotrodes are in bevelled form, the bevelled end part of the outer suction sonotrode 17 converging in the direction of the axis whilst the bevelled end part of the internal irrigation sonotrode 14 has a diverging form.

The different positions that the sonotrodes may occupy with respect to each other, as well as their forms, have different effects on the tissues and thus on the efficiency of the apparatus.

In the case illustrated in FIG. 2a, i.e. when the ends of the two sonotrodes are located in the same transverse plane, it is possible to obtain an effect of fragmentation which is localized and on the surface.

In the case illustrated in FIG. 2b, i.e. when the internal irrigation sonotrode 14 passes beyond the outer suction sonotrode 17, the vibrations of the two sonotrodes 14 and 17 are phase-shifted with respect to one another due to their different diameters, which has for its effect to obtain with the suction a phenomenon of shear of the tissues.

In the case illustrated in FIG. 2c, i.e. when the irrigation sonotrode 14 is located inside the suction sonotrode 17 itself, a veritable tissular lysis is obtained which alters nothing in the selective cut of the vibrating instrument 2 at its end.

Thanks to the configuration with two sonotrodes 14 and 17 which has been described hereinabove, a combined effect is obtained of two instruments with ultrasound vibrations which reinforces the cavitation and avoids, to be very efficient, having to increase the power of the transducer or of the suction. In order to be able to clear the vision of the operative field, it is possible to arrange for the axis of the vibrating instrument 2 no longer to be aligned with the axis of the hand-piece 1, as is shown in FIG. 1, but for it to form therewith an angle which may range from 0° to 90° with intermediate adaptation pieces to be connected. A straight intermediate extension may also be employed between the hand-piece 1 and the instrument 2.

FIGS. 3 and 4 show a simplified variant of a hand-piece 1 obtained thanks to the use of the piezo-electricity. In this case, the transducer 5 uses, in place of a piezo-electric tube, an assembly of pellets 22 mounted in series and tightened against one another by means of an axial tie-rod 23 and nuts 23a. As the transducer 5 forms a compact assembly without possibility of passage therethrough, the irrigation conduit 24 and the suction conduit or conduits 25 are still provided inside the hand piece 11, but outside the transducer 5. More particularly, as may be seen more readily in FIG. 4, the suction conduit 25 and irrigation conduit 24 are housed in the space available between the transducer 5 and the cylindrical wall 26 of the hand-piece 1.

In the variant embodiment illustrated in FIG. 5, the apparatus according to the invention comprises a single sonotrode 27 for suction and irrigation, which is mechanically coupled, as in the preceding cases, to the transducer housed in the hand-piece 1. This single sonotrode 27 presents, on its lateral surface, one or more longitudinal grooves which enable the irrigation liquid to go, under the effect of the ultrasounds, as far as the end of the sonotrode. At that point, the liquid is sucked inside the sonotrode 27 with the debris taken along, and the suction current flows axially inside the sonotrode 27 and through a conduit in the hand-piece 1 up to the suction connector. Supply of irrigation liquid is effected by means of an annular connecting piece 28 which is fixed on the front end of the hand-piece 1 and which surrounds the base of the sonotrode 27, leaving a free passage 29 between the connecting piece 28 and the base of the sonotrode 27. This passage enables the irrigation liquid, which is conducted by a tube 30 opening out inside the connecting piece 28, to flow on the longitudinal grooves of the sonotrode 27 in the direction of the end thereof.

FIG. 6 shows a variant embodiment of a single sonotrode 31 for suction and irrigation which presents, on its lateral surface, at least one helical thread 32 channelling the flow of the irrigation liquid which, as in the preceding case, goes, under the effect of the ultrasounds, in the direction of the end of the sonotrode 31.

In the variant embodiment illustrated in FIG. 7, the single sonotrode 33 for suction and irrigation comprises a hollow rod, of slightly conical form, of which the central axial conduit is connected, through the hand-piece, to the suction connector and which bears, on its lateral surface, one or more longitudinal irrigation tubes 34.

In the variant embodiment of the invention shown in FIG. 8, the apparatus which has been illustrated and described with reference to FIG. 1 is provided with a third coaxial sonotrode 35 which surrounds the suction sonotrode 17, itself containing the irrigation sonotrode 14. This third sonotrode 35 forms an integral part of a base 36 which bears a tube 37 for connection to a source of irrigation fluid and which is fixed, by any appropriate means and with interposition of a seal 38, on the front part of the transducer 5. Such a device offers the advantage of allowing the path of several treatment liquids over a zone to be treated and this principle is particularly interesting when it is necessary to place these liquids into presence at the last moment.

Furthermore, the apparatus according to the invention makes it possible also to transmit, right through the hand-piece 1 and the vibrating instrument 2, a beam of hot light in order to obtain, for example, an immediate haemostasis. A bipolar sonotrode with diathermic effect as well as a laser beam may be used, each of these effects being able to be combined.

We claim:

1. Ultrasound apparatus for the curettage or exeresis of biological tissues by irrigation of a liquid subjected to cavitation and by suction of the disaggregated tissue, comprising:
   a hand-piece containing a transducer which is mechanically coupled to a sonotrode;
   a suction conduit within said hand-piece having a front end and a rear end and extending therebetween in a longitudinal direction in said hand-piece;
   a suction connector at the rear end of said hand-piece and connected to the rear end of said suction conduit;
   a suction sonotrode in said hand-piece connected to the front end of said suction conduit; and
   means traversing longitudinally right through said hand-piece and said sonotrode for allowing the transmission therethrough of at least one of a beam of hot light for illumination and/or of a cutting laser beam, for treatment or haemostatis.

2. An ultrasound apparatus for the curettage or exeresis of biological tissues by irrigation of a liquid subjected to cavitation and by suction of the disaggregated tissue, comprising:
   a hand-piece containing an ultrasonic transducer;
   two coaxial vibrating sonotrodes mechanically coupled to said transducer, said sonotrodes having front ends located in planes transverse to said hand-piece, and rear ends connected respectively to a suction connector and to an irrigation conduit means including a pair of conduits extending longitudinally in a space provided between the transducer and a wall of said handpiece.

3. Apparatus according to claim 2, wherein one of said sonotrodes is an inner irrigation sonotrode while the other of said sonotrodes is an outer suction sonotrode.

4. Apparatus according to claim 2, said irrigation conduit means extends longitudinally right through said hand-piece.

5. Ultrasound apparatus for the curettage or exeresis of biological tissues by irrigation of a liquid subjected to cavitation and by suction of the disaggregated tissue, comprising:
   a hand-piece containing a transducer which is mechanically coupled to a vibrating instrument;
   a suction conduit within said hand-piece having a front end and a rear end and extending therebetween in a longitudinal direction is said hand-piece;
   a suction connector at the rear end of said hand-piece and connected to the rear end of said suction conduit;
   sonotrode means in said hand-piece connected to the front end of said suction conduit for suctioning; and
   means longitudinally traversing through said vibrating instrument for allowing the transmission therethrough of a beam of hot light for illumination and/or of a cutting laser beam, for treatment or haemostatis.

6. Apparatus according to claim 5, wherein said sonotrode means includes a single suction and irrigation sonotrode, and irrigation conduit means extending over the surface of said single suction and irrigation sonotrode, and said conduit means being connected to the interior of a connecting piece fixed on the front part of said hand-piece, and a tube connected to said connecting piece for connecting said connecting piece to a source of irrigation fluid, said connecting piece defining with the base of said single suction and irrigation sonotrode a passage for the irrigation fluid towards the front end of said vibrating instrument.

7. Apparatus according to claim 2, wherein said vibrating instrument is a sonotrode.

8. Apparatus according to claim 5, wherein said single suction and irrigation sonotrode bears, on its lateral surface, longitudinal grooves ensuring the path of the irrigation fluid.

9. Apparatus according to claim 5, wherein said single suction and irrigation sonotrode bears, on its lateral surface, at least one helical thread guiding the path of the irrigation fluid.

10. Apparatus according to claim 5, wherein said single suction and irrigation sonotrode bears, on its lateral surface, at least one longitudinal tube ensuring flow of the liquid of the irrigation fluid.

11. Apparatus according to claim 5, wherein said sonotrode means comprises at least two coaxial sonotrodes, one of said sonotrodes being an outer suction sonotrode and the other being an internal irrigation sonotrode.

* * * * *